United States Patent [19]

McCapra

[11] Patent Number: 5,321,136
[45] Date of Patent: Jun. 14, 1994

[54] PERI SUBSTITUTED FUSED RING CHEMILUMINESCENT LABELS AND THEIR CONJUGATES, AND ASSAYS THEREFROM

[75] Inventor: Frank McCapra, Seaford, Great Britain

[73] Assignee: London Diagnostics, Inc., Eden Prairie, Minn.

[21] Appl. No.: 860,410

[22] Filed: Mar. 30, 1992

Related U.S. Application Data

[63] Continuation-in-part of Ser. No. 140,040, Dec. 31, 1987, abandoned, Ser. No. 291,843, Dec. 29, 1988, abandoned, and Ser. No. 418,956, Oct. 10, 1989, abandoned.

[51] Int. Cl.⁵ .......................................... C07D 215/14
[52] U.S. Cl. .................................. 546/104; 436/501; 530/409; 544/355; 546/61; 546/79; 546/93; 546/102; 546/107; 546/108; 546/112; 546/147; 546/170
[58] Field of Search .............. 546/79, 93, 102, 104, 546/107, 108, 61, 112, 147, 170; 544/355; 436/501; 530/409

[56] References Cited

U.S. PATENT DOCUMENTS

| | | | |
|---|---|---|---|
| 3,352,791 | 11/1967 | Sheehan et al. | 546/102 X |
| 3,689,391 | 9/1972 | Ullman | 546/102 X |
| 4,745,181 | 5/1988 | Law et al. | 546/104 X |
| 4,918,192 | 4/1990 | Law et al. | 546/104 |
| 4,946,958 | 8/1990 | Campbell et al. | 546/104 |
| 4,950,613 | 8/1990 | Arnold et al. | 546/104 |
| 5,110,937 | 5/1992 | Law et al. | 546/102 |

FOREIGN PATENT DOCUMENTS

| | | | |
|---|---|---|---|
| 216553 | 4/1987 | European Pat. Off. | 546/102 |
| 324202 | 7/1989 | European Pat. Off. | 546/102 |
| 330050 | 8/1989 | European Pat. Off. | 546/104 |
| 361817 | 4/1990 | European Pat. Off. | 546/102 |
| 1461877 | 1/1977 | United Kingdom | 546/102 |

*Primary Examiner*—Richard L. Raymond
*Attorney, Agent, or Firm*—George A. Skoler

[57] ABSTRACT

A chemiluminescent label compound and conjugate containing the same, in which the compound involves a fused ring system comprising a (i) hetercyclic ring as a fused member thereof in which the heterocyclic ring contains
   (a) one or more nitrogen heteroatoms in the ring;
   (b) at least one saturated or unsaturated ring in fused state with the heterocyclic ring;
   (c) an available carbon atom in the heterocyclic ring that is adjacent to a carbon forming a fused ring with the heterocyclic ring; and
   (d) at least one substituent that is peri relative said available carbon of the heterocyclic ring, which substituent serves to enhance the hydrolytic stability of the chemiluminescent label compound; and (ii) a leaving group coupled to the heterocyclic ring through a carbon adjacent to a fused ring carbon such that the leaving group and heterocyclic ring join to form a difunctional carboxy-containing linkage in which the carboxy carbon is directly bonded to the carbon of the heterocyclic ring adjacent to a fused ring carbon,
   (a) the linkage being an ester, thiolester or amide of a carboxylic acid, and
   (b) said linkage substituted heterocyclic ring is susceptible to chemical attack to dissociate the heterocyclic ring to a transient compound by first cleaving the linkage to dissociate the leaving group from the heterocyclic ring system followed by dissociation of the residual carbonyl from the linkage.

Also described are assays and assay kits that employ such label compounds.

49 Claims, No Drawings

PERI SUBSTITUTED FUSED RING CHEMILUMINESCENT LABELS AND THEIR CONJUGATES, AND ASSAYS THEREFROM

RELATED APPLICATIONS

This application is a continuation-in-part of application Ser. No. 140,040, filed Dec. 31, 1987, now abandoned copending application Ser. No. 291,843, filed Dec. 29, 1988, now abandoned and copending application Ser. No. 418,956, filed Oct. 10, 1989, now abandoned.

BRIEF DESCRIPTION OF THE INVENTION

This invention relates to unique chemiluminescent labeling compounds, conjugates containing associated versions of the labeling compounds, assays and kits for performing such assay utilizing the conjugates. The labeling compounds contain special sterically-hindered heterocyclic esters, thiolesters and amides.

BACKGROUND TO THE INVENTION

The literature describes classes of compounds that give off light or "luminesce" by reaction through chemical treatment. The compounds that have this capability are termed chemiluminescent materials. Their dissociation is typically caused by treatment with peroxide or molecular oxygen at high pH. Light is produced by the decay of the transient ("intermediate") structure formed by peroxide or molecular oxygen reaction at an $sp^2$ or $sp^3$ hybridized carbon in the compound that is part of a chain or a ring or ring system.

As the literature indicates, any series of reactions which produce the intermediate:

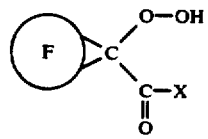

will lead to moderate to strong chemiluminescence. (F) is a structure such that the product carbonyl derivative

is fluorescent and X is a good leaving group, usually with XH, for efficient chemiluminescence, having a $pK_a$ of about $\leq 11$, preferably $<11$, and most preferably, from about 5 to about 8. The reaction may require base catalysis.

The intermediate can be prepared (in isolable or transient form, depending on (F)) from species such as:

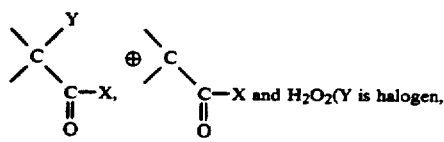

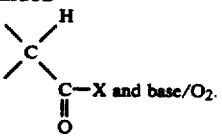

See *Endeavour*, 23, No. 117 (1973) p. 140, *The Chemistry of Bioluminescence* in "*Bioluminescence in Action*" (P. J. Herring, ed.), Academic Press, London, 1978 (pp. 64-5), *Proc. R. Soc. Lond.*, B 215, p. 256 (1982), *Progress in Organic Chemistry*, (W. Carruthers and J. K. Sutherland, eds.), Butterworth, London (1973), p. 261, all authored by F. McCapra.

For example, chemiluminescent aryl esters that contain such hybridized carbon, termed a labeling compound, react according to the following general reaction:

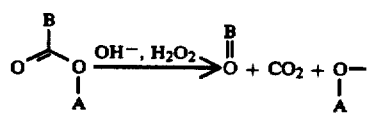

where A is an aryl ring or ring system and B is a heterocyclic ring or ring system. In this reaction, —O—A, the leaving group, is cleaved by perhydrolysis resulting in steps leading to the transient intermediate, B=O, that proceeds to decay generating luminescence.

The characteristics of some of these chemiluminescent compounds, their chemistry of manufacture, and other factors relating to them, are more fully described by McCapra, "Chemiluminescence of Organic Compounds," in Progress in Organic Chemistry, vol. 8, Carruthers and Sutherland ed., Wiley & Sons (1973); Kohen, Bayer, Wilechek, Barnard, Kim, Colleins, Beheshti, Richardson and McCapra, "Development Of Luminescence-Based Immunoassays For Haptens And For Peptide Hormones," pp. 149-158, in *Analytical Applications Of Bioluminescence and Chemiluminescence*, Academic Press, Inc. (1984); Richardson, Kim, Barnard, Collins and McCapra, *Clinical Chemistry*, vol. 31, no. 10, pp. 1664-1668 (1985); McCapra, "The Application of Chemiluminescence in Diagnostics," 40th Conference of the American Association of Clinical Chemists, New Orleans, La., Jul. 28, 1988; McCapra, "The Chemiluminescence Of Organic Compounds," Quarterly Reviews, vol. 20, pp. 485-510 (1966); McCapra, "The Chemiluminescence Of Organic Compounds," *Pure and Applied Chemistry*, vol. 24, pp. 611-629 (1970); McCapra, "The chemistry of bioluninescence," *Proceedings Of Royal Society*, vol. B215, pp. 247-278 (1982); McCapra and Behesti, "Selected Chemical Reactions That Produce Light," *Bioluminescence and Chemiluminescence; Instruments and Applications*, CRC Press, vol. 1, Chapter 2, pp. 9-37 (1985); McCapra, "Chemiluminescent Reactions of Acridines," Chapt. IX, *Acridines*, R. M. Acheson, Ed., pp. 615-630, John Wiley & Sons, Inc. (1973); McCapra, "Chemical Mechanisms in Bioluminescence," *Accounts Of Chemical Research*, vol. 9, no. 6, pp. 201-208 (June 1976); and in many other publications and presentations on the subject.

As noted in the above literature, chemiluminescent compounds of a variety of structures have been projected as labels in a variety of assays including immunoassays (in this respect, see U.S. Pat. Nos. 4,383,031, 4,380,580 and 4,226,993). The esters, thiolesters and amides, alone or conjugated (i.e., chemically coupled to another material), are especially desirable forms of chemiluminescent labels. However, they lose their luminescence capability over time in an aqueous system because they hydrolyze to products that are not available to the assay. Until recently, these compounds have not been used in commercial assays. Until the invention of copending application Ser. No. 07/859,995, now U.S. Pat. No. 5,284,952 the ester, thiolester and amide forms of this class of materials lacked sufficient hydrolytic stability to be stored in the most convenient form, which is as a component of an aqueous system.

Carboxylic acid esters, thiolesters and amides are susceptable to hydrolytic attack resulting in the formation of the carboxylic acid and the hydroxy, mercapto or amino component that is the theoretical or actual precursor to the ester, thiolester or amide. It is recognized that some amount of hydrolytic attack can be inhibited by the inclusion of bulky groups that chemically sterically hinder those linkages, see Nishioka, et al., *J. Org. Chem.*, vol. 40, no. 17, pp. 2520–2525 (1975), Fujita et al., "The Analysis of the Ortho Effect," *Progress in Physical Organic Chemistry*, 8, pp. 49–89 (1976), Morrison and Boyd, *Organic Chemistry*, 5th Ed., pp. 842–843 (1987) and March, *Advanced Organic Chemistry*, 3rd Ed., page 240 (1985). According to March:

"Another example of steric hindrance is found in 2,6-disubstituted benzoic acids, which are difficult to esterify no matter what the resonance or field effects of the groups in the 2 or the 6 position. Similarly, once the 2,6-disubstituted benzoic acids are esterified, the esters are difficult to hydrolyze." (Emphasis in the original)

The difficulty in esterification is not the same in making esters from 2,6-substituted phenols, but the general principles described by March are applicable to enhancing the hydrolytic stability of the resultant ester so long as the ortho substitutions are electron donating.

The position of the bulky sterically hindering group relative to the linkage is important for retarding hydrolysis. Groups that may be dormant to any other reaction may not provide steric hindrance because of its chemical nature. For example, a group in a position alpha to a carbonyl moiety of an ester group that is electron withdrawing (such as an alpha chloro group) could adversely affect the hydrolytic stability of the ester group. Thus, the relative position of the bulky group and its chemical nature is important if steric hindrance depends on the presence of such group in the molecule.

The function of chemiluminescent labels in assay applications involves the coupling of the label compound to a substrate molecule. Such coupling can be achieved by solvent interraction (e.g., molecular compatibility), any heterolytic or homolytic mechanism induced by chemical means and influenced by physical effects, such as time, temperature and/or mass action. For example, the reaction can be nucleophilic or electrophilic, or it can involve free radical mechanisms. In the broadest perspective, the coupling can be viewed as achievable via strong to weak bonding forces.

A chemiluminescent label in assays is an associated moiety of a binding material. The moiety is derived from a chemical compound which, as such, possesses chemiluminescent capabilities. Hereinafter, the term moiety as applied to the label as such, is a reference to the compound prior to being associated with a binding material. The term associated is intended to include all or any of the mechanisms for coupling the label to the substrate molecule.

The term "functional" in chemistry typically refers to a group that influences the performance of a chemical or constitutes the site for homolytic or heterolytic reactions. For example, a functional alkyl substituent, used in the context of interreactions through that substituent, means an alkyl group substituted so that it can effect that reaction. But an alkyl group termed functional for the electronic effects it induces in the molecule is a reference to the alkyl group per se.

THE INVENTION

This invention relates to unique chemiluminescent labeling compounds, conjugates containing associated versions of the labeling compounds, assays and kits for performing such assay utilizing the conjugates. The labeling compounds contain peri substituted[1] sterically-hindered heterocyclo esters, thiolesters and amides.

[1] Webster's Third New International Dictionary, Unabridged: "having substituents in or relating to positions 1 and 8 in two fused 6-membered rings (as in napthalene)"

This invention relates to novel chemiluminescent labeling compositions and their conjugates with specific binding materials. These compositions and the conjugates find special application in specific binding assays because the chemiluminescent compound, i.e., the labeled moiety, has surprisingly enhanced stability in aqueous solutions coupled with exceptional light emmitting qualities.

The root compound of the invention is a chemiluminescent label compound characterized by a fused ring system containing a hetercyclic ring as a fused member thereof, and a leaving group coupled to the heterocyclic ring through a carbon adjacent to a fused ring carbon. The leaving group and heterocyclic ring join to form a difunctional carboxy-containing linkage in which the carboxy carbon is directly bonded to the carbon of the heterocyclic ring adjacent to a fused ring carbon. Illustrative linkages include ester, thiolester or amide of a carboxylic acid. The linkage substituted heterocyclic ring is susceptible to chemical attack (such as oxidic attack) to form a transient compound from the heterocyclic ring by first cleaving the linkage to dissociate the leaving group from the heterocyclic ring system followed by dissociation of the residual carbonyl from the linkage. In a specific illustration, the heterocyclic ring is ring carbon-bonded to the carbonyl of an ester, thiolester and amide moiety and possesses a heteroatom in an oxidation state that allows chemiluminescence by dissociating a compound ("intermediate") that decays to produce chemiluminescence, at the heterocyclic ring carbon bonded to the carbonyl.

A preferred fused ring system comprises: a heterocyclic ring containing one or more nitrogen heteroatoms in the ring; at least one saturated or unsaturated ring in fused state with the heterocyclic ring; an available carbon atom in the heterocyclic ring that is adjacent to a carbon forming a fused ring with the heterocyclic ring; and at least one substituent that is peri relative said available carbon of the heterocyclic ring, which substituent serves to enhance the hydrolytic stability of the chemiluminescent label compound.

In the case of this invention, the choice of the leaving group is not as critical as it is in the prior art because the hydrolytic stability of the chemiluminescent label is not dependent upon the leaving group's chemical characteristics. There are a wide variety of leaving groups suitable in the practice of this invention. The choice of any of them may be arbitrary, if desired, but generally, economics and/or performance will be the dictating criteria for the selection of leaving group. The preferred leaving group has a $pK_a$ of about $\leq 11$, in accordance with the literature.

In a preferred embodiment of the invention, the leaving group includes an aryl ring or ring system. The aryl ring or ring system is ring carbon-bonded to the other end of the linking oxygen, sulfur or nitrogen of the ester, thiolester or amide, as the case may be. The aryl ring may be unsubstituted or substituted. When substituted, the substitution may be chemically or electronically functional. In a most preferred embodiment, the aryl ring or ring system contains at least one substituent on a six-member ring. The substituent on the six-member ring may be one or more groups acting in concert with peri substitution on the heterocyclic ring system to sterically and electronically hinder hydrolysis of the ester, thiolester or amide linkage. In selecting such aryl group substituent(s) it is desirable to use one or more ortho substituent groups, alone or in conjunction with meta and/or para substituents that possess a specific level of electron withdrawing capacity. That specific level of electron withdrawing capacity is a $\sigma_p$ value greater than 0 and less than 1. This last combination causes the chemiluminescent label compound to have uniquely high hydrolytic stability.

Also in accordance with the present invention are conjugates of the labeling composition, assay systems utilizing the conjugates, and assay kits incorporating such chemiluminescent labels.

In particular, this invention relates to a hydrolytically stable heterocyclic composition capable of chemiluminescent properties when labeled (i.e., affixed as a label) to a specific binding material by chemically-induced dissociation, comprising (a) a sterically-hindered ester, thiolester or amide linkage moiety with enhanced hydrolytic stability,
(b) a leaving group that comprises a portion of (a),
(c) a heterocyclic organic ring moiety that comprises a portion of (a), in which
  (1) the carbonyl carbon of (a) is covalently bonded to a carbon atom (x) of (c) and the remaining free valence of (a) is carbon bonded to (b), and
  (4) (c) contains
    (i) at least one ring carbon atom adjacent to said ring carbon atom (x),
    (ii) a bulky group in a position peri to (x) and
    (ii) a ring member heteroatom in an oxidation state that provides such chemiluminescence properties.

Also, this invention contemplates hydrolytically stable conjugates possessing chemiluminescent properties by chemical dissociation, comprising a chemiluminescent label bonded to a specific binding material that contains (a) a sterically-hindered ester, thiolester or amide linkage moiety with enhanced hydrolytic stability,
(b) a leaving group that comprises a portion of (a),
(c) a heterocyclic organic ring moiety that comprises a portion of (a), in which
  (1) the carbonyl carbon of (a) is covalently bonded to a carbon atom (x) of (c) and the remaining free valence of (a) is carbon bonded to (b), and
  (4) (c) contains (i) at least one ring carbon atom adjacent to said ring carbon atom (x),
  (ii) a bulky group in a position peri to (x) and
  (iii) a ring member heteroatom that is in an oxidation state whereby reaction of molecular oxygen or a peroxide with said composition forms an intermediate which decays to produce chemiluminescence.

The invention encompasses a method for assaying the presence of an analyte in a sample. The method comprises contacting an analyte with the aforementioned chemiluminescent-labeled specific binding material (the "conjugate"), inducing chemiluminescence by decay of an intermediate dissociated from the conjugate, and measuring luminescence therefrom to assay the analyte.

In keeping with the inventive chemiluminescent-label's function of assaying, the invention embodies a specific binding assay kit comprising a vial containing a conjugate possessing chemiluminescent properties by chemically induced dissociation and containing the aforementioned chemiluminescent label bonded to a specific binding material.

In a preferred embodiment of the invention, the chemiluminescent label is a compound that possess organofunctionality that allows it to chemically couple to a substrate, such as a specific binding material (e.g., proteins). Such organofunctionality is provided in the chemiluminescent label compound either as part of the leaving group or the heterocyclic moiety. Typically, the organofunctionality is a group that is reactive with a complementary group on the substrate specific binding material. That means that the groups interreact homolytically or heterolytically, preferably via a nucleophilic reaction, to form a reaction product of the chemiluminescent label bonded to the substrate.

DETAILED DESCRIPTION OF THE INVENTION

Desirable chemiluminescent labeling compounds of the present invention include compositions encompassed by the following formula:

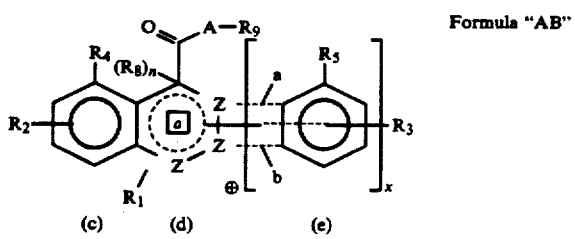

Formula "AB"

In this formula AB, ⊡ denotes the optional saturated or unsaturated nature of the internal heterocyclic ring shown in hatched lines. When n is 1, ⊡ is characterized by saturation, in which the ring in question is devoid of aromatic unsaturation. When n is 0, ⊡ is characterized by unsaturation, in which the ring is question is aromatically unsaturated. That distinction in unsaturation is further characterized by the following:

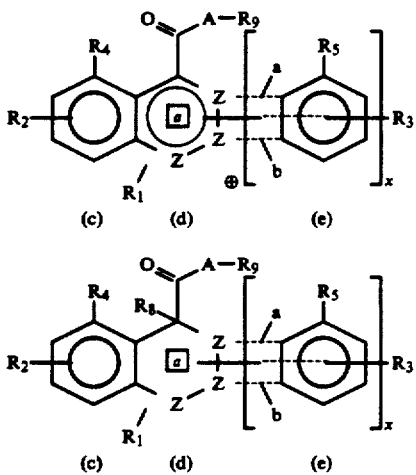

In the above formulae "A" and "B", ▣ characterizes specific unsaturated (formula "A") or saturated (formula "B") forms. $R_8$ may be hydrogen. Formulas AB, as well as "A" and "B", depict ring systems comprising at least two fused rings; in this case, rings designated "(c)", "(d)" and optionally "(e)". Two (2) of the Z's are carbon, and one (1) Z is nitrogen. Where the Z is carbon, it is bonded to one hydrogen unless it is part of a fused ring or contains a pendant group. Ring (e) may be a fused ring, in which case bonds a and b represent common carbons shared by both rings (d) and (e) and the proximate or adjacent Z's represent the shared carbons. Ring (e) may be a pendant ring attached to ring (d) by a convalent carbon to carbon bond represented by bonds a or b, depending upon where the pendancy occurs. The presence of ring (e) is determined by the value of x, which is either 0 or 1.

Peri substituents, which can cause peri-interactions, include any group which can cause steric hindrance with respect to the carbon to which the ester, thiolester or amide linkage is attached and/or with respect to the carbon within the ester, thiolester of amide linkage. Preferred peri substituents include short alkyl groups (such as $C_{1-4}$, e.g., methyl, ethyl, and the like), aryl groups (e.g., phenyl), alkaryl (e.g., tolyl, xylyl, and the like), alkoxyalkyl (where the alkyls thereof contain $C_{1-4}$, e.g., methoxymethyl, ethoxyethyl, and the like). The peri substituents, if present, are located on carbon atoms within the heterocyclic ring or ring system which are "adjacent to" the carbon to which the ester, thiolester or amide linkage is attached. Moieties can include more than one peri substituent. For example, peri substituents can be placed in the following positions:

(a) in acridiniums and acridans: on $C_1$ and $C_8$;
(b) in phenanthridiniums and reduced phenanthridiniums: on $C_7$; and
(c) in quinoliniums and reduced quinoliniums: on $C_3$.

Of the peri groups, $R_4$ and $R_5$ (when ring (e) is fused with ring (d)), $R_4$ is a bulky steric-hindering group and $R_5$ is a bulky steric-hindering groups or hydrogen. Preferably, both are steric-hindering groups. When ring (e) is a fused ring with ring (d), and $R_5$ is hydrogen, it is desirable that $R_9$ comprise an aryl group having at least one electron-donating substitutent in an ortho position thereof relative to linkage to the —COA— moiety. ($R_1$—) is an organo group that is carbon to nitrogen bonded to the Z that is nitrogen. $R_2$— and $R_3$— are organo groups or hydrogen bonded to ring carbon atoms of rings (c), (d) and (e), as the case may be. When $R_2$— or $R_3$— are organo groups, they are bonded to ring carbon, preferably by a carbon to carbon bond, carbon to oxygen bond, carbon to nitrogen bond, carbon to sulfur bond, and the like. In addition, $R_2$— and $R_3$— may be amino, substituted amino, hydroxy, halogen, carboxy, or sulfonyl (and their esters).

"A", in the above formulas, may be —O—, —S— or —NT—, and with $R_9$ form the leaving group. The leaving group possesses the typical $pK_a$ of about $\leq 11$. T is a stable nitrogen bonded group such as —$SO_2CF_3$, to form —$N(SO_2CF_3)$—, and equivalent groups. Methods for forming such —NT— groups are described by Maulding et al., "Chemiluminescence from Reactions of Electrophilic Oxamides with Hydrogen Peroxide and Fluorescent Compounds," *J. Org. Chem.*, 33, 1, 250–254, (1968); Tseng et al., *J. Org. Chem.*, 44, 4113 (1979); Mohan, U.S. Pat. No. 4,053,430; Tseng et al., European Pat. Appln. 811 003 69.8 (1981); and European Pat. Applns. Pub. Nos. 0 273 115 and 0 257 541.

$R_9$ may be a variety of organo groups bonded to A by a carbon bonded thereof. $R_9$ may be a variety of groups, such as alkyl (preferably $C_{1-12}$), aryl (preferably phenyl, naphthyl and anthracyl), aralkyl (preferably where the aryl is phenyl, and the alkyl is $C_{1-12}$), alkaryl (preferably where the aryl is phenyl, and the alkyl is $C_{1-12}$), substituted alkyl (preferably $C_{1-12}$), substituted aryl (preferably phenyl, naphthyl and anthracyl), substituted aralkyl and substituted alkaryl (preferably where the aryl groups are phenyl and the alkyl groups are $C_{1-12}$), in which the substituents provide (i) functionality for coupling the compound to a substrate containing a complementary functional group and/or (ii) functional groups that are electron donating and/or withdrawing and enhance the hydrolytic stability of the compound when conjugated with a specific binding material.

A variety of functional groups are suitable, in accordance with this invention, for use as $R_9$ functional groups. Illustrative are the following groups bonded directly or indirectly to the organo group:

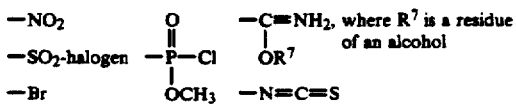

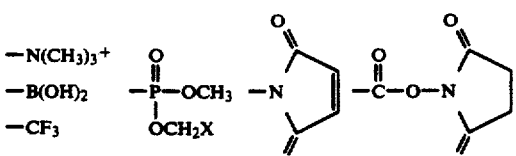

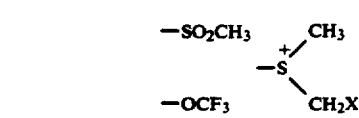

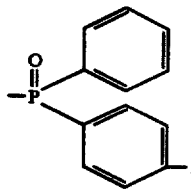 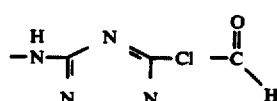
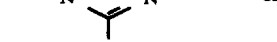

—N₃ and other photolabile functionalities

Preferably, R₉ is aryl of the formula:

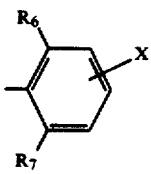

in which $R_6$ and $R_7$ may be hydrogen, alkyl ($C_{1-4}$), alkoxy or alkyl sulfide, part of a fused ring system, with alkyl and alkoxy being preferred when one of $R_4$ or $R_5$ is hydrogen. X may be a variety of electron withdrawing groups, particularly the above illustrated functional groups, to wit,

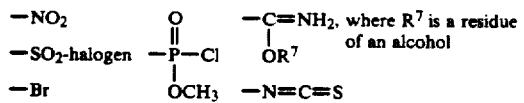

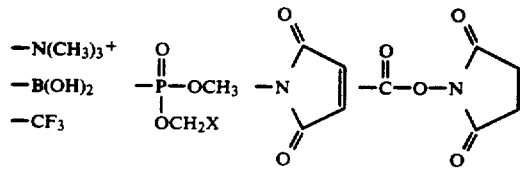

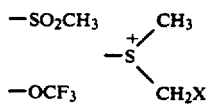

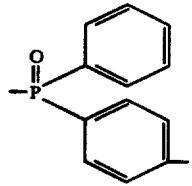

—N₃ and other photolabile functionalities preferably such functional groups as nitro, halogen, carboxy, carboxamido, sulfonamide, sulfonyl halide and the like, preferably having a $\sigma_p$ value greater than 0 and less than 1. Electron donating groups may also be chosen for X to provide kinetic properties suitable for particular assays. The preferred groups are —NO₂, —SO₂Cl, —Br, and —N(CH₃)₃⁺. Most preferred are —NO₂ and —SO₂Cl, the former for the uniquely high hydrolytic stability it confers to the label, per se or when conjugated, and the latter for the exceptional bonding to proteins, forming high $\sigma_p$ value stable sulfonamide bonds, and the superior hydrolytic stability conferred to the label, per se, or when conjugated.

Covalent coupling the chemiluminescent label to a substrate may also be effected through reaction of functional groups contained in R₁, R₂ or R₃ that are complementary to the functional group(s) present in the substrate, e.g., the specific binding material. In most cases, coupling will occur as a result of a nucleophilic reaction between the chemiluminescent label and the substrate resulting in chemical linkage of the chemiluminescent label to the substrate. The choice chemical linkage is typically the result of the reaction of an organofunctional group on the substrate that contains an active hydrogen with a complementary functional group present in the chemiluminescent label compound that reacts with the active hydrogen containing group. Illustrative of such functional groups reactive with the active hydrogen containing group includes the following:

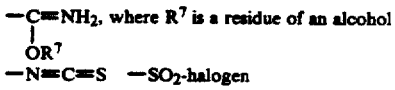

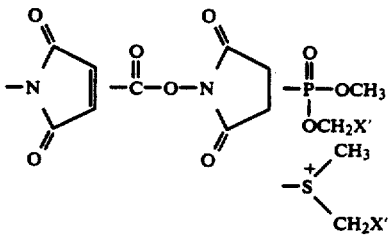

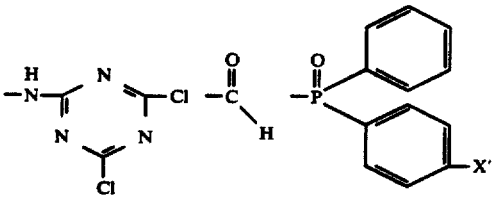

—N₃ and other photolabile functionalities in which halogen may be fluorine, chlorine, bromine and iodine, chlorine being the most preferred, and X' is a functional group reactive with active hydrogen or carboxylic acid derivative, such as carboxyl halide, sulfonyl halide, amino and other groups known to be suitable for a linking reaction to proteins, nucleic acids and small molecule analytes. In addition, the functionality may be in the form of amino, mercapto, hydroxy, bonded to alkyl and aryl moieties. In the case of R₂ and 3 groups, they may comprise aryl groups that are directly joined to the heterocyclic ring or ring system or indirectly joined by a number of units, such as oxy, sulfide, sulfoxide, sulfone, amino, alkylene, alkenylene, alkynylene, alkylamino and aminoalkyl, to illustrate a few. The following illustration of functional groups encompass a number of those defined above as well as some additional ones that can be included in R₂ and 3 groups:

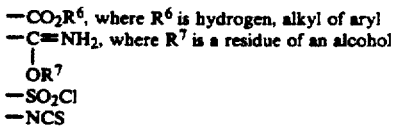

-continued

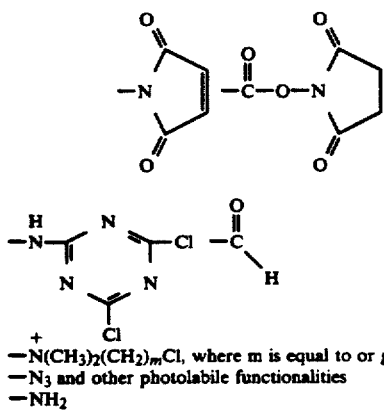

—$N(CH_3)_2(CH_2)_mCl$, where m is equal to or greater than 1
—$N_3$ and other photolabile functionalities
—$NH_2$ or oniums (such as quaternary ammoniums, phosphoniums, sulfoniums, and the like), sugars, polyalkylenepolyamines and polyalkyleneoxide (e.g., polyoxyethylene, polyoxy-1,2-propylene, polyoxy-1,3-propylene, polyoxy-1,2-butylene, etc.), and the like. Other chains, groups and functionalities useful for attaching compounds of the present invention via $R_{1,2,3 \text{ or } 9}$ group reactions to protein are discussed in Ji, "Bifunctional Reagents," Meth. Enzymology 91:580 (1983), which is incorporated herein by reference. Methods of joining such attaching groups to protein and other materials utilize both covalent bonding and weaker chemical forces, and are well known in the art.

In addition, $R_1$, $R_2$, and $R_3$ may comprise organo groups that provide a number of advantages, such as operating as surface active agents in compatibilizing the label compound or its conjugate in aqueous medium or to antigen structures. For example, they may comprise —$(CH_2CH_2O)_nY$, where n=1-10, and Y can be hydrogen, alkyl, and the like.

The label compounds of formula AB, including formulae A and B, comprise a heterocyclic ring (d) or ring system (c), (d) and (e) to which the ester, thiolester or amide linkage -CO-A- is attached at a carbon atom within the heterocyclic ring or ring system. That carbon atom (1) is either $sp^2$ or $sp^3$ hybridized, as shown in the two formulas, and (2) is susceptible to attack by peroxide or molecular oxygen to form the intermediate that decays to produce chemiluminescence. The oxidation state of the heteroatom within the heterocyclic ring or ring system will determine whether the carbon atom is susceptible to such attack. If the carbon to which the linkage is attached is $sp^2$ hybridized, the heteroatom is in a positive oxidation state (i.e., have a positive charge, for example, as obtained by N-alkylation or N-oxidation). If the carbon to which the linkage is attached is $sp^3$ hybridized, the heteroatom is in a neutral oxidation state (i.e., uncharged). When the heteroatom is nitrogen, proper oxidation states can be achieved only if the nitrogen is substituted with an alkyl group (including a reactive functionalized alkyl group), an aryl group (including a reactive functionalized aryl group), —O— (if the nitrogen is in a positive oxidation state) or —OH (if the nitrogen is in a neutral oxidation state). When the heteroatom is in these "proper" oxidation states, the carbon atom will be susceptible to attack by peroxide or molecular oxygen to produce the chemiluminescent intermediate.

Heterocyclic rings or ring systems that contain the heteroatom in a positive oxidation state include without limitation the following fused ring systems: acridinium, benz[a]acridinium, benz[b]acridinium, benz[c]acridinium, a benzimidazole cation, quinolinium, isoquinolinium, quinolizinium, a cyclic substituted quinolinium, phenanthridinium, and quinoxalinium. Rings or ring systems in which the heteroatom is in a neutral oxidation state include the reduced forms of the foregoing. These rings or ring systems are derived from the following rings or ring systems:

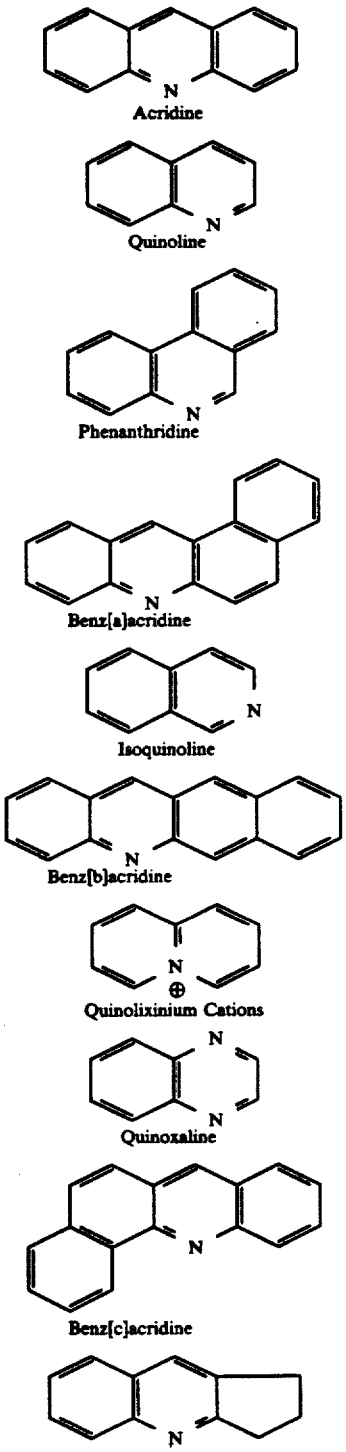

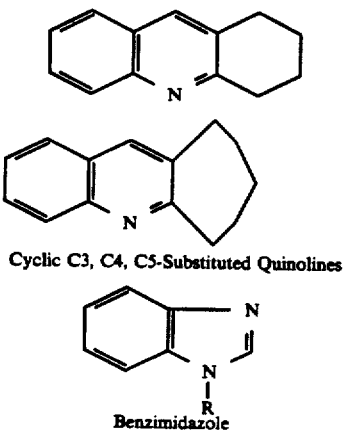

Cyclic C3, C4, C5-Substituted Quinolines

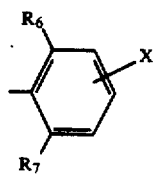

Benzimidazole

The aryl ring or ring system, represented by

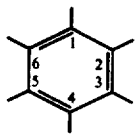

includes at least one substituted six-member ring of the formula

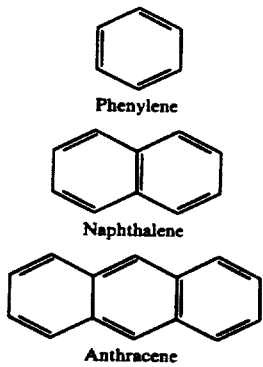

in which the substituents comprise at least one X at ring carbons 3, 4 and 5. The ester, amide or thioester linkage is directly attached through a covalent bond to such six-member ring at ring carbon 1. The ring may include but is not limited to phenyl, naphthyl and anthracyl, which are derivatives of the following structures:

Phenylene

Naphthalene

Anthracene

In those cases where napthyl or anthracyl rings are employed, one of the rings constitutes the core structure of $R_9$ and the other ring or rings are formed in combination with any adjacent set of ring carbons thereof other than carbon 1. The above aryl linked through carbon 1 may be substituted at any aromatic carbon position provided carbon atoms 2 and 6 are appropriately substituted when one of $R_4$ and $R_5$ is hydrogen. In that case, it is preferred that one or more of carbons 3, 4 and 5 are appropriately substituted with a group having a $\sigma_p$ value greater than 0 and less than 1.

$R_6$ and $R_7$ are the classic bulky electron donating groups which are located on aryl group at $C_2$ and $C_6$ so as to sterically hinder, in the traditional manner, the hydrolysis of the linkage between aryl group and the heterocyclic ring or ring system. Where the aryl is phenyl with an ester linkage being attached at position 1, $R_6$ and $R_7$ are located at the ortho 2 and 6 positions. $R_6$ and $R_7$ may be the same or different, and either may include, when they are not hydrogen:

an alkyl (such as $C_{1-4}$) or optionally functionalized alkyl (such as $C_{1-4}$) group an aryl (such as described above) or optionally functionalized aryl group —OR, where R is alkyl (such as $C_{1-4}$) or aryl (such as described above) —SR, where R is alkyl (such as $C_{1-4}$) or aryl (such as described above).

The required steric hindrance can also be provided by other rings within a multi-ring unit comprising $R_9$ which are "adjacent" to the six-member ring to which the A group is attached. For example, if the aryl is naphthyl and an ester linkage is attached at the 1 position, $R_6$ or $R_7$ could be hydrogen at the 2 position and the other is the "adjacent" ring containing carbons 7-10. In such cases, the adjacent ring is considered, in the classic sense of steric hindrance, to be an electron donating substituent (on the six-member ring within $R^3$) which sterically hinders the hydrolysis of the linkage.

The peri substituted heterocyclics of the invention are first generated by the reaction of an isatin of the formula:

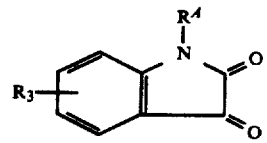

in which $R^4$ is hydrogen, phenyl, $R_2$ substituted phenyl, alkyl and the like, with itself or with an acetophenone or phenol of the formulae:

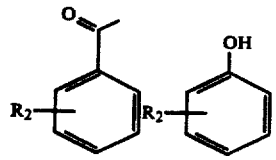

in which $R_2$ and $R_3$ are described above. Details of such reactions are set forth below. The resulting carboxylic acid is converted to the acid chloride by reaction with, e.g., thionyl chloride or phosphorus trichloride. Esterification, amidation or thioesterification may be effected in the usual manner as taught in the art.

In many cases, the reactions will proceed to the formation of intermediates that require separation for the next reaction step or final products that require isolation. In such cases, conventional techniques such as distillation, extraction, crystallization, washing and the like, will be required. Conventional separation by the addition of non-solvent to a solvent solution to force precipitation of a desired material is frequently found useful.

The above-described improved chemiluminescent compounds are useful in a broad range of specific binding assays for the presence of analyte in a sample. "Presence" shall mean herein the qualitative and/or quantitative detection of an analyte. Such assays may be directed at any analyte which may be detected by use of the improved chemiluminescent compound in conjunction with specific binding reactions to form a moiety thereon. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes a chemiluminescent conjugate which comprises the improved chemiluminescent moiety attached to a specific binding material. "Specific binding material" means herein any material which will bind specifically by an immunoreaction, protein binding reaction, nucleic acid hybridization reaction, and any other reaction in which the material reacts specifically with a restricted class of biological, biochemical or chemical species. In this category of assays, the chemiluminescent conjugate participates in a specific binding reaction and the presence of analyte in the sample is proportional to the formation of one or more specific binding reaction products containing the chemiluminescent conjugate. The assay is performed by allowing the requisite specific binding reactions to occur under suitable reaction conditions. The formation of specific binding reaction products containing the chemiluminescent conjugate is determined by measuring the chemiluminescence of such products containing the chemiluminescent conjugate or by measuring the chemiluminescence of unreacted or partially reacted chemiluminescent conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent moiety is attached, is capable of specifically binding with the analyte. The assay further utilizes a reactant which is capable of specifically binding with the analyte to form a reactant-analyte-chemiluminescent conjugate complex. The reactant may be attached to a solid phase, including without limitation, dip sticks, beads, tubes, paper or polymer sheets. In such cases, the presence of analyte in a sample will be proportional to the chemiluminescence of the solid phase after the specific binding reactions are completed. Such assay formats are discussed further in U.S. Pat. Nos. 4,652,533, 4,383,031, 4,380,580 and 4,226,993, which are incorporated herein by reference.

In a competitive format, the assay utilizes a reactant which is capable of specifically binding with the analyte to form an analyte-reactant complex and with the specific binding material, to which the chemiluminescent moiety is attached, to form a chemiluminescent conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the chemiluminescence of the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-chemiluminescent conjugate complex formed as a reaction product. This is illustrated by attaching the chemiluminescent moiety to an antibody which is specific to a surface antigen on a cell. The presence of the cell surface antigen will be indicated by the chemiluminescence of the cells after the completion of the reaction. The cells themselves may be used in conjunction with a filtration system to separate the analyte-chemiluminescent conjugate complex which is formed on the surface of the cell from unreacted chemiluminescent conjugate. This is discussed further in U.S. Pat. No. 4,652,533.

The improved chemiluminescent moiety may be used in additional assay formats known in the art including without limitation sequential saturation and competitive displacement, both of which utilize a chemiluminescent conjugate where both (1) the specific binding material, to which the moiety is attached, and (2) the analyte specifically bind with a reactant. In the case of sequential saturation, the analyte is reacted with the reactant first, followed by a reaction of the chemiluminescent conjugate with remaining unreacted reactant. In the case of competitive displacement, the chemiluminescent conjugate competitively displaces analyte which has already bound to the reactant.

In a quenching format, the assay utilizes a reactant which is capable of specifically binding with the analyte to form an analyte-reactant complex and with the specific binding material, to which the chemiluminescent moiety is attached, to form a chemiluminescent conjugate-reactant complex. A quenching moiety is attached to the reactant. When brought into close proximity to the chemiluminescent moiety, the quenching moiety reduces or quenches the chemiluminescence of the chemiluminescent moiety. In this quenching format, the presence of analyte is proportional to the chemiluminescence of the chemiluminescent moiety. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the chemiluminescent conjugate may be reacted with the complex on the solid phase. Alternatively, the solid phase, sample and chemiluminescent conjugate may be added together simultaneously and reacted prior to separation. As a still further but less preferred alternative, the analyte in the sample and the chemiluminescent conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated improved chemiluminescent compound. The presence of analyte in the sample is proportional to the formation of one or more specific binding reaction products which do not themselves contain the chemiluminescent moiety. Instead, the chemiluminescent compound chemiluminesces in proportion to the formation of such reaction products.

In one example of this second category of assays, the assay utilizes a reactant capable of binding with the analyte to form an analyte-reactant complex which causes the chemiluminescent compound to chemiluminesce. This is illustrated by a simple enzyme-substrate assay in which the analyte is the substrate glucose and the reactant is the enzyme glucose oxidase. Formation of the enzyme-substrate complex triggers the chemiluminescent compound. Such enzyme-substrate assay for glucose is disclosed in U.S. Pat. Nos. 3,964,870 and 4,427,770, both of which are incorporated herein by reference. This enzyme-substrate assay is a specific binding assay in the sense that the substrate specifically binds to the active site of the enzyme in much the same way that an antigen binds to an antibody. In this assay, the enzyme specifically binds with the substrate which results in the production of peroxide which, in turn, causes the chemiluminescent compound to chemiluminesce.

Also included in the second category of assays are those assays in which the formation of the reaction products promotes or inhibits chemiluminescence by the chemiluminescent compound in a less direct manner. In this assay, a first reactant, which is cross reactive with the analyte, is attached to an enzyme such as glucose oxidase close to its active site. A second reactant which is specific for both the analyte and the immunoreactive material is added to the sample and the altered enzyme in the presence of the substrate (i.e., glucose). When the second reactant binds to the first reactant located near the active site on the enzyme, the second reactant blocks the active site in a way that the substrate cannot bind to the enzyme at the active site or the binding of the substrate at the active site is significantly decreased. The second reactant blocking the enzyme in this manner inhibits the enzyme from producing peroxide which, in turn, would have triggered the chemiluminescent moiety. Analyte in the sample, however, will tie up the second reactant, thus preventing the second reactant from inhibiting the production of peroxide. The presence of analyte will be proportional to the chemiluminescence of the compound.

The assays contained in the above two categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-chemiluminescent conjugate complex is separated from unreacted chemiluminescent conjugate. In a surface antigen assay, the analyte-chemiluminescent conjugate complex is separated form unreacted chemiluminescent conjugate. In a competitive assay, the reactant-chemiluminescent conjugate complex is separated from unreacted chemiluminescent conjugate. In a sequential saturation assay and in a competitive displacement assay, the reactant-chemiluminescent conjugate complex is separated from unreacted chemiluminescent conjugate. Alternatively, in homogeneous assays the reaction products are not separated. After the assay reagents have been allowed to react, the chemiluminescence may be measured from the whole assay mixture whether such mixture is in solution, on a solid phase or distributed between various membrane layers of a dip stick or other solid support. The glucose assay using glucose oxidase and a chemiluminescent moiety illustrates a simple homogeneous assay in which separation is unnecessary. The quenching assay illustrates a more complex homogeneous assay in which separation is unnecessary. It is contemplated that either category of assay formats may give rise to either heterogeneous or homogeneous formats.

Finally, "measuring the chemiluminescence" shall include, where relevant, the act of separating those specific binding reaction products, the formation of which are proportional to the presence of analyte in the sample, from other reaction products. It shall also include, where relevant, the acts of (i) treating the chemiluminescent moiety with acid to cleave a $R_8X$ group from the moiety, and/or (ii) triggering the chemiluminescent moiety to chemiluminesce in the case of those assay formats in which the formation of the reaction products does not itself trigger the chemiluminescent moiety.

The following procedure, specific for chemiluminescent labels similar to those of the invention, for attaching (conjugating) to protein is generally applicable to chemiluminescent labels of the present invention.

Mouse IgG (Sigma, 1 mg) dissolved in 0.9 ml phosphate buffer (100 mM, pH 8.0, 150 mM or to higher pH, such as a pH as high as 9.5) is divided into three equal portions of 0.33 mg/0.3 ml (0.0022μmoles). About 0.3 mg of a conjugate of the present invention is dissolved in about 0.4 ml DMF so as to obtain 0.022 μmoles of moiety in 15 μl DMF.

0.022 μmoles of the compound of the present invention is mixed with 0.0022 μmoles of IgG in a plastic microcentrifuge tube. After 15 minutes, an additional 0.022 μmoles of compound is added to the microcentrifuge tube (compound to protein molar ratio was 20:1). After an additional 15 minutes, excess amounts of the compound of the present invention are quenched with lysine HCl solution (10 ml in 100 mM p/buffer, pH 8.0) for 15 minutes.

Alternatively, aliquots of 0.0055 mmoles of the compound of the present invention is used instead of 0.022 μmoles (compound to protein molar ratio was 5:1).

Biorad glass columns (1 cm × 50 cm) (commercially available from Biorad, Chemical Division, Richmond, Calif.) are packed with previously swelled and deaerated Sephadex G-50-80 in phosphate buffer (100 mM, pH 6.3, 150 mM NaCl, 0.001% TMS) to a bed volume of 45 ml. The reaction solution is run through the columns at a flow rate of 0.3–0.4 ml/min. 0.5 ml fractions are collected. Labelled protein fractions detected by diluting 20 μl from each fraction to 1 ml are used to determine the chemiluminescence produced with 30 μl of the diluted solution. Labelled fractions are then pooled.

The pooled conjugate fractions, to improve the purity of immunoreactive conjugate, is dialyzed against 500 ml pH 6.3 phosphate buffer (100 mM, pH 6.3, 150 mM NaCl, 0.001% TMS) over a period of 24 hours with three buffer changes.

General labeling procedure for sulfonyl chloride based acridinium esters

Anti-TSH antibody (1 mg) is transferred to a Centricon 30 (ultrafiltration unit, Amicon, Beverly, Mass.) and 1 ml bicarbonate buffer (15 mM, pH 9.6) is added. The buffer is centrifuged and the volume of solution brought up to 400 μl using the same buffer. A solution of the labeling compound of the invention in DMF (N,N-dimethylformamide)[2] is added to the anti-TSH antibody and the Centricon is gently mixed for 15 minutes by hand. Another 21.6 μl from a freshly made DMF solution of the same compound, is added at the end of 15 minutes. A total of 24 moles pf the compound to antibody, is used in the reaction. Fifteen minutes from the second addition, the protein solution is purified from the unreacted compound using a Sephadex desalting column (Pharmacia HR-10/10), an HPLC system, and a eluent solvent comprising 1 part ethanol and 4 parts phosphate buffer (100 mM sodium phosphate, 300 mM sodium chloride, pH 6.0). The protein fraction is collected and the eluent solvent is exchanged with phosphate buffer (pH 6.3) in a Centricon 30. The concentrate acridinium labelled anti-TSH antibody is diluted into 25 ml of diluent buffer (sodium phosphate buffer 100 mM, sodium chloride 150 mM, Thimerosal 0.001%, 0.4% BSA, 0.1 mg/ml each (0.001%) of mouse and goat γ-globulins, pH 6) after filtration through a 0.45 micron syringe filter. The diluted 25 milliliters is stored at −20° C. as a stock solution to make TSH labelled antibody reagent after appropriate dilutions.

[2] 2 mg/mL, 21.6 μl in the case of (2,6-dimethyl-3-chlorosulfonyl)phenyl-N-methyl-acridinium-9-carboxylate fluorosulfonate]

ASSAY PROTOCOLS

In making assays encompassed by the invention, there may be employed the following general protocols, characterized in terms of chemiluminescent label similar to those of the invention. These procedures are applicable to the practice of this invention.

1. Components

A) Labelled Antibody (conjugate): Affinity purified rabbit anti-prolactin conjugated to (2,6-dimethoxy-3-chlorosulfonyl)phenyl-N-methyl-acridinium-9-carboxylate fluorosulfonate. Storage buffer: 10 mM phosphate buffer, 100 mM NaCl pH 6.0, 0.001% Thimerosal, 0.4% BSA.

B) Capture antibody: Rabbit anti-prolactin (6 μg/ml) as a solid phase on Nunc tubes (commercially available from Midland Scientific, Roseville, Minn.).

C) Solid-phase coated tubes: Dried Nunc tubes were prepared as follows:
1) 0.3 ml of the capture antibody per tube at 6 μg/ml in PBS buffer (phosphate buffer saline, pH 7.2–7.4, 10 mM phosphate, 100 mM NaCl, 10 mM NaN₃) was pipetted into Nunc tubes.
2) Tubes were incubated for 18–24 hours.
3) Tubes were washed 2 times with the PBS buffer.
4) Tubes were blocked with 2.0% BSA in PBS buffer. Incubate for <4 hours at room temperature.
5) Tubes were washed 3 times with PBS buffer.
6) Tubes were dried at room temperature.
7) Tubes were stored in plastic freezer bags at 4° C.

D) Standards: Prepared in horse serum 0, 5, 30, 100 and 200 ng/ml/ml

2. Assay Protocol
1) 25 μl of sample or standard was pipetted into the antibody-coated tubes.
2) 100 μl of labelled antibody was added.
3) Tubes were vortexed gently.
4) Tubes were incubated for 1 hour at room temperature on a rotator.
5) Tubes were washed 3 times with deionized water.
6) Chemiluminescence was counted for 2 seconds [pump 1: 0.1N HNO₃ + 0.25% H₂O₂; pump 2: 0.25N NaOH + 0.125% CTAC] in a LumaTag ™ Analyzer (commercially available from London Diagnostics, Eden Prairie, Minn.).

Assay for TSH:
1. Components

A) Labelled Ab: Affinity purified goat anti-TSH was conjugated to (2,6-dimethoxy-3-chlorosulfonyl)phenyl-N-methyl-acridan-9-ethoxy-9-carboxylate as follows: a solution of the anti-TSH antibody (approximately 100 μg) in bicarbonate buffer (0.1M, pH 9.6) was treated with 25 moles excess of (2,6-dimethoxy-3-chlorosulfonyl)phenyl-N-methyl-acridan-9-ethoxy-9-carboxylate as a solution in DMF. The reaction mixture was purified on a fast flow Sephadex G25 (superfine) column (Pharmacia, infra) using an HPLC system. The protein peak was collected at a flow rate of approximately 0.75 ml/min with a mobile phase of phosphate buffer (pH 6.0) containing approximately 20% ethanol. After buffer exchange the labelled antibody preparation was diluted with storage buffer to provide approximately 100,000 counts/100 μl in a LumaTag ™ Analyzer after 1:10 dilution.

B) Storage buffer: 100 mM phosphate, 0.145M NaCl, 0.001% Thimerosal, 0.4% BSA, 0.1 mg/ml mouse γ-globulins, and 0.1 mg/ml goat γ-globulins, pH 6.0.

C) Capture antibody: Monoclonal-anti-TSH (2 μg/ml) as a solid phase on Nunc tubes. Procedure for preparation of solid-phase Nunc tubes:
1) 0.4 ml of the capture antibody at 2 μg/ml in PBS buffer (phosphate buffer saline, pH 7.2–7.4, 10 mM phosphate, 100 mM NaCl, 10 mM NaN₃) was added to each tube.
2) Tubes were incubated for 18–24 hours.
3) Tubes were washed 3 times with the PBS buffer.
4) Tubes were blocked with 2.0% BSA in PBS buffer and incubated for <4 hours at room temperature.

5) Tubes were washed 3 times with PBS buffer.
6) Tubes were dried at room temperature.
7) Tubes were stored in plastic freezer bags at 4° C.

D) Standards: Prepared in horse serum.0, 0.05, 0.1, 0.5, 2.5, 10, 25 and 50 μIU/ml E) Wash Solution: saline buffer containing BSA 2. Assay Protocol
1) 200 μl of sample was pipetted into the coated tubes.
2) 100 μl of labelled antibody was added.
3) Tubes were vortexed gently.
4) Tubes were incubated for 2 hours at room temperature on a shaker.
5) 1 ml Wash Solution was added to each tube.
6) Tubes were washed using a Biotomic washer (commercially available from Ocean Scientific, Inc., Garden Grove, Calif.).
7) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.).

Addition of $HNO_3$ to the assay mixture containing the labeled antibody causes the $C_9$ ethoxy group to cleave from the acridinium molecule before the chemiluminescent reaction is triggered by the addition of NaOH.

SYNTHESIS OF MOIETIES

The following examples show the synthesis of certain chemiluminescent moieties of the present invention. These chemiluminescent moieties are typically made in small quantities and the procedures employed for their manufacture do not reflect conventional large scale chemical manufacturing procedures. In these reactions, conventional reactions have been employed to produce the chemiluminescent labels of the invention. Purification procedures suitable for isolating product are conventional laboratory procedures, such as crystallization out of solvent solution by the addition of a nonsolvent, solvent extraction, and the like. In such cases, many different solvents and nonsolvents are suitable. Yields are the amounts recovered as a percentage of reactants employed.

EXAMPLE 1

Preparation of (2,6-dimethoxy) phenyl-1,3-dimethyl-acridinium-9-carboxylate fluorosulfonate. The acridine carboxylic acid

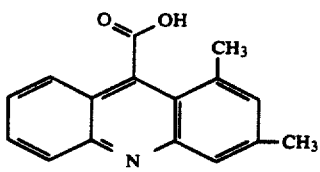

esterified with (2,6-dimethoxy) phenol by Brewster method (J. H. Brewster, et al., *J. Org. Chem.*, 77: 6214 (1953) incorporated herein by reference), is purified in a silica gel column and treated with methylfluorosulfonate gave the acridinium ester

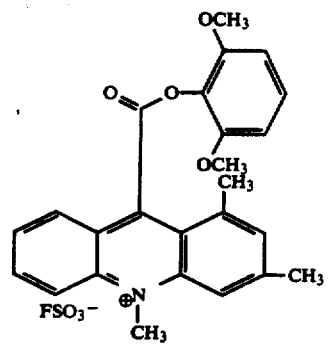

EXAMPLE 2

The procedure of Example 1 was repeated with 2-methoxy-phenol to obtain

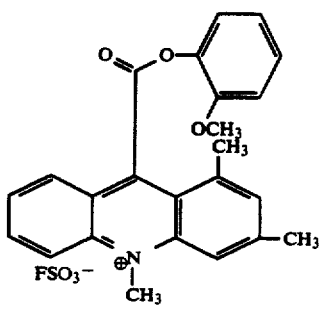

EXAMPLE 3

The compound 4'-(2-Succinimidyloxy carbonyl ethyl)phenyl-1,3-dimethyl-N-methyl-acridinium-9-carboxylate fluorosulfonate was prepared as follows. The following acridine acid

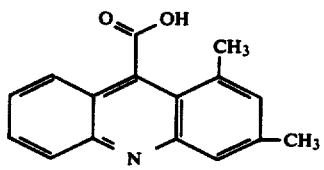

was synthesized by condensation of isatin and 3,5-dimethyl aniline. The acridine acid was esterified with 3-(4-hydroxyphenyl) propionic acid benzyl ester by the aforementioned Brewster method and the product was purified on a silica gel column. The benzyl protective group was removed by treatment of

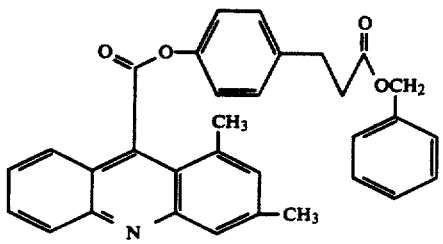

with HBr/acetic acid to obtain

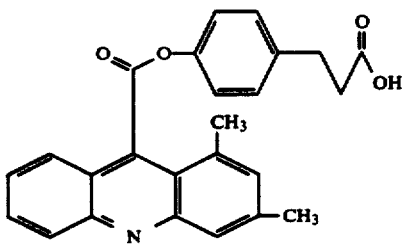

The N-hydroxysuccinimide ester

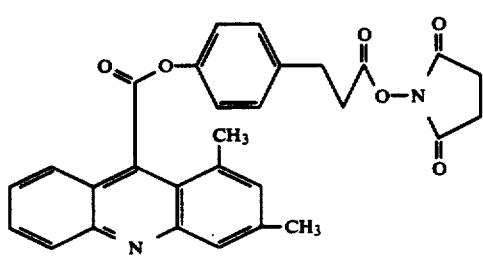

was obtained by treating the foregoing acid with dicyclohexyl carbodiimide in DMF and N-hydroxysuccinimide. The ester was methylated with methyl fluorosulphate in methylene chloride to obtain

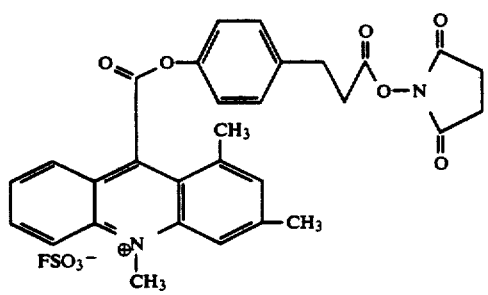

FAB mass spectrum for this moiety: m/e is 511 ($C_3OH_{27} O_6 N_2$). The compound was conjugated to TSH polyclonal antibody and the labeled antibody was purified on a fast desalting column (Sephadex). The acridinium labeled antibody was tested in a Luma-Tag ™ system (London Diagnostics, Inc., Eden Prairie, Minn.). Stability was tested over a 60-day period and compared similar to that of the same TSH polyclonal antibody labeled with the conjugate of (2,6-dimethoxy-3-chlorosulfonyl)phenyl-N-methyl-acridinium-9-carboxylate fluorosulfonate.

EXAMPLE 4

Preparation of phenyl-N-methyl-1,3-dimethyl-acridinium-9-carboxylate fluorosulfonate of the formula:

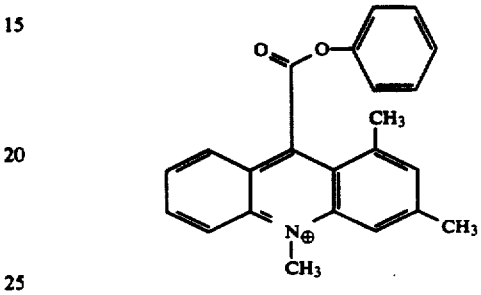

Phenyl-N-methyl-1,3-dimethyl-acridan-9-methoxy-9-carboxylate was synthesized from phenyl-N-methyl-1,3-dimethyl-acridinium-9-carboxylate according to HPLC as described above. To produce phenyl-N-methyl-1,3-dimethyl-acridinium-9-carboxylate, 3,5-dimethylaniline and bromobenzene were reacted under extention Ulmann reaction conditions to obtain the N-phenyl-N-(3,5-dimethyl)phenylamine. Reaction of N-phenyl-N-(3,5-dimethyl)phenylamine with oxalyl chloride provided the intermediate N-phenyl-dimethyl isatin. Upon cyclization under basic conditions, the 1,3-dimethyl-acridine-9-carboxylic acid was formed. The acridine phenyl ester was formed by esterification with phenol as previously described. Phenyl-N-methyl-1,3-dimethyl-acridinium-9-carboxylate was produced from the acridine ester as described above.

EXAMPLE 5

The precursor compound 1,3,6,8 tetramethylacridine-9-carboxylic acid was prepared according to the following set of reactions:

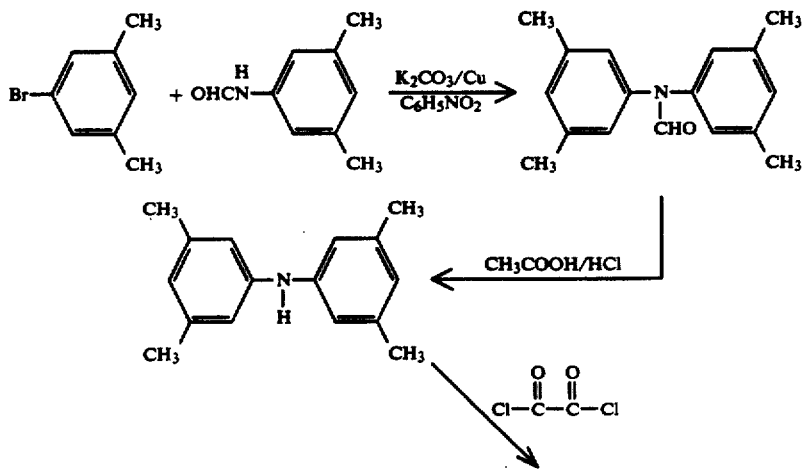

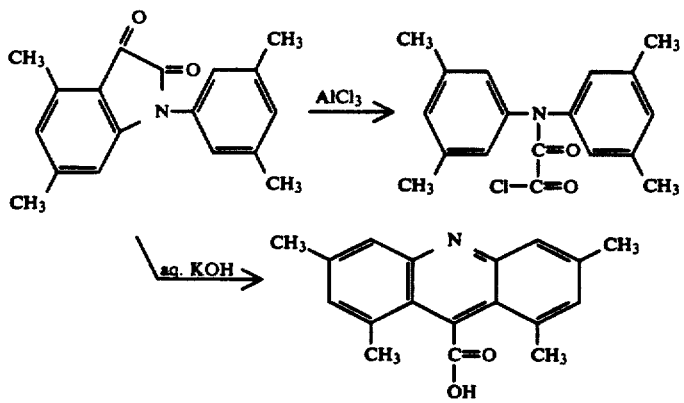

Tetramethyldiphenylamine, from the reaction of N-formyl-3,5-dimethylaniline and 5-bromo-m-xylene, as indicated above, was obtained in fairly high yield (55%).

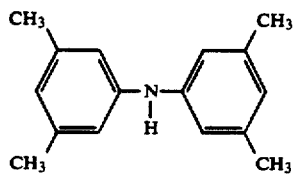

was treated with oxalyl chloride and then aluminium chloride to give the isatin

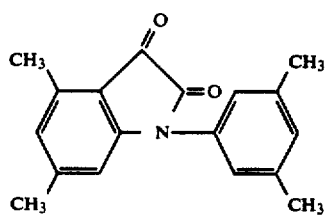

as a red solid in about an 80% yield. It was characterized as follows:

microanalysis, Theory: 77.42%C; 6.09%H; 5.02%N; Found: 76.99%C; 6.13%H; 4.93%N.

IR(Nujol) shows carbonyl peaks at 1738 cm.$^{-1}$ and 1714 cm.$^{-1}$.

In the last step, 1,3,6,8-tetramethylacridine-9-carboxylic acid was prepared from the isatin in aqueous potassium hydroxide with 85% yield. It was characterized by IR, M.S. and NMR.

IR(Nujol) shows carbonyl peak at 1753 cm.$^{-1}$

M.S.(FAB) shows peak at 280$^m$/e (M$^+$ +1)

NMR (360 FT,d$_6$DMSO) shows aromatic peaks from 7.47 ppm to 7.34 ppm and two singlets at 3.02 ppm and 2.49 ppm for methyl groups.

the route to 1,3,6,8-tetramethyl-4-chlorosulfonylphenyl-N-methylacridinium-9-carboxylate fluorosulfonate is shown in the following:

Step 1

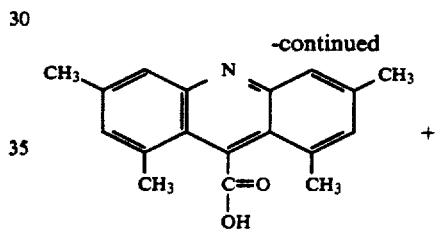

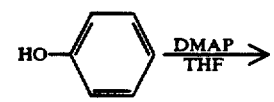

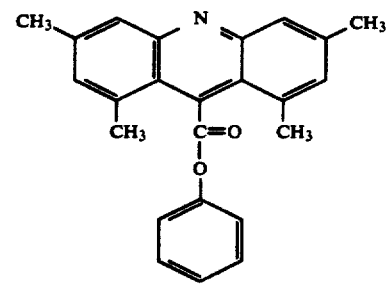

Step 2

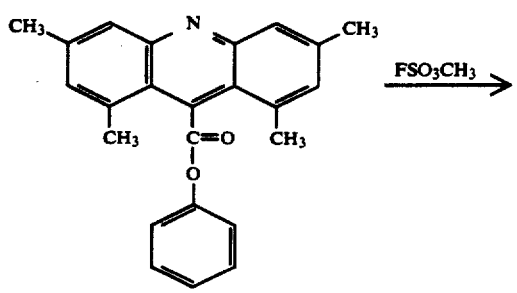

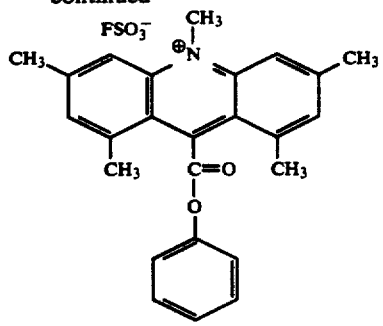

Step 3

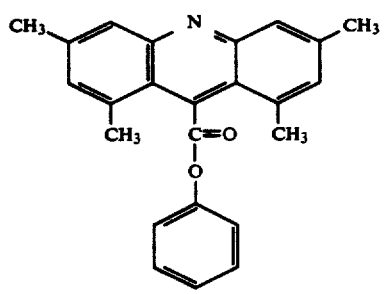

In step 1, 1,3,6,8 tetramethylacridine-9-carboxylic acid was esterified with phenol in THF and 4-dimethylamino-pyridine [DMAP]. Phenyl-1,3,6,8-tetramethylacridine-9-carboxylate was obtained in about 55% yield after recrystallization from benzene.

IR(Nujol) shows carbonyl peak at 1761 Cm.−1
M.S.(FAB) shows peak at 356$^m$/e (M$^+$ +1)
NMR (360 MH$_2$,CDCl$_3$,δ) shows aromatic peaks from 7.9188 ppm to 6.86 ppm and two singlets for methyl groups at 2–83 ppm and 2.51 ppm.

Phenyl-1,3,6,8-tetramethylacridine-9-carboxylate was N-methylated (step 2) with methylfluorosulfonate to give

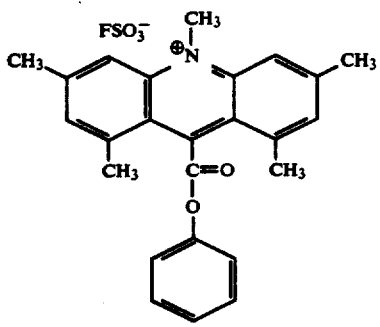

Phenyl-1,3,6,8-tetra-methyl-N-methylacridinium-9-carboxylate fluorosulfonate in 80% yield.

M.S.(FAB) shows peak at 371$^m$/e (M$^+$ +1)

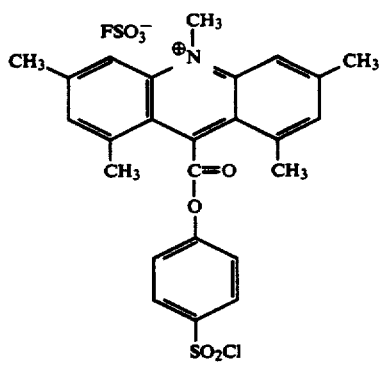

The above compound, 4-chlorosulfonylphenyl-1,3,6,8-tetramethyl-N-methylacridinium-9-carboxylate fluorosulfonate, was prepared from

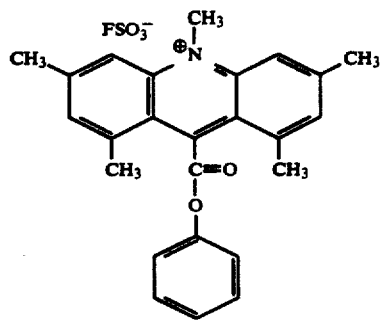

using chlorosulfonic acid and thionylchloride in about 60% yield (step 3).

Stability Study 1

The two compounds:

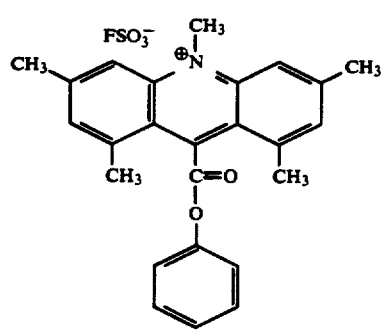

"Compound A"

and

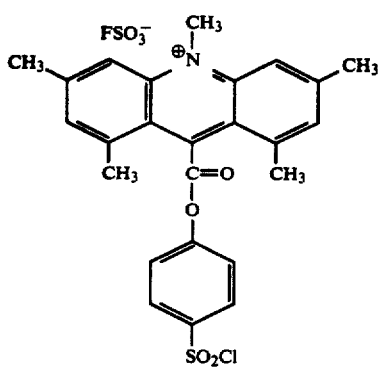

"Compound B"

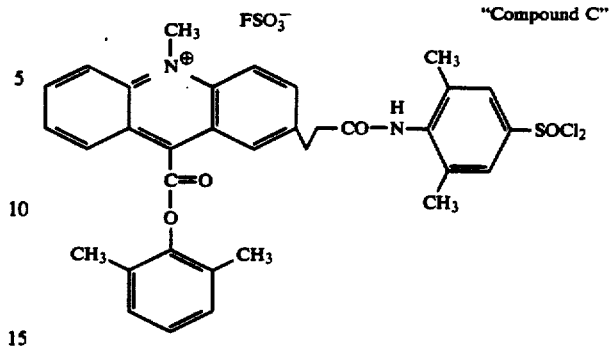

"Compound C"

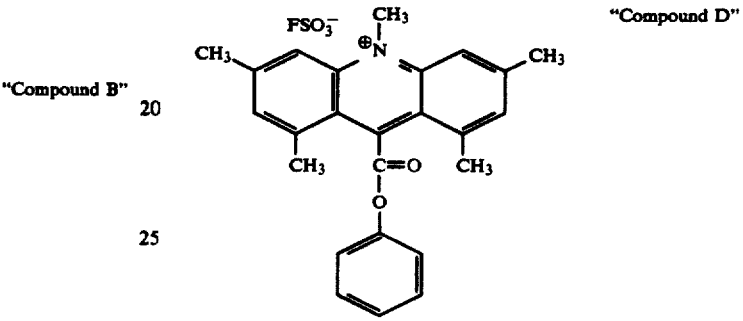

"Compound D"

were tested for hydrolytic stability. After purification, Compounds A and B were diluted to 6.25 ml with diluent buffer solution and used as stock solutions. They were diluted to 1,200,000, 1,000,000 and 800,000 for 100 μl and used for TSH assay. The results showed fairly high stabilities for both compounds. In the following tables, "RLU" means relative light units, measured with a LumaTag ™ system (London Diagnostics, Inc., Eden Prairie, Minn.).

|   | Hours | COMPOUND A*/RLU | % Recovery A* | COMPOUND B*/RLU | % Recovery B* |
|---|---|---|---|---|---|
| 1 | 0.00 | 312000 | 100 | 284500 | 100.000 |
| 2 | 24.00 | 370707 | 119 | 324131 | 114.000 |
| 3 | 48.00 | 410511 | 132 | 289869 | 102.000 |
| 4 | 72.00 | 377831 | 121 | 274029 | 96.000 |
| 5 | 144.00 | 349592 | 112 | 269315 | 95.000 |
| 6 | 168.00 | 322003 | 103 | 245407 | 86.000 |
| 7 | 198.00 | 300721 | 96 | 235807 | 83.000 |
| 8 | 222.00 | 290071 | 93 | 230032 | 81.000 |

Stability Study 2

Using the procedure set forth above, anti-TSH antibodies labeled with and compared with a commercial label of a TSH conjugate,

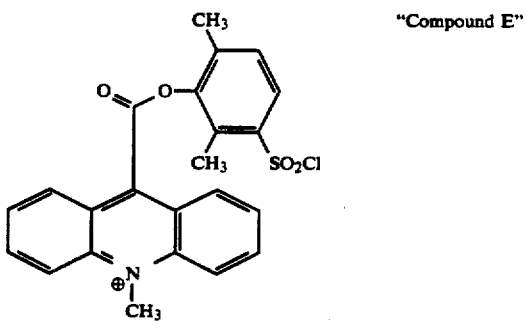

"Compound E"

were tested for hydrolytic stability. After purification, the compounds were diluted to 6.25 ml with diluent buffer solution and used as stock solutions. They were diluted to 1,200,000, 1,000,000 and 800,000 for 100 μl and used for TSH assay.

TSH assays were carried out according to the procedures described above. Adequate results for higher concentration of TSH standards were obtained.

| Time Hrs. From 0 | Compound C | | Compound D | | Compound E | |
|---|---|---|---|---|---|---|
|  | RLU | % REC | RLU | % REC | RLU | % REC |
| 0.00 | 312000 | 100 | 281500 | 100 | 367000 | 100 |
| 19.60 | 302486 | 97 | 193819 | 69 | 333583 | 91 |
| 26.60 | 310263 | 99 | 190463 | 68 | 345139 | 94 |
| 47.50 | 287979 | 92 | 176114 | 63 | 325428 | 89 |
| 91.00 | 265341 | 85 | 161033 | 57 | 300274 | 82 |
| 116.00 | 267360 | 86 | 148951 | 53 | 293458 | 80 |
| 139.00 | 255013 | 82 | 133338 | 47 | 286770 | 78 |
| 163.00 | 240179 | 77 | 128892 | 46 | 275909 | 75 |

EXAMPLE 6

The acid chloride (300 mg, 1.008 mmoles)

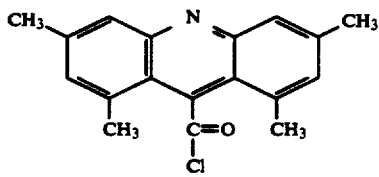

was mixed with o-cresol (150 mg., 1.39 mmoles), 4-dimethylaminopyridine (12 mg., 0.0984 mmoles) and triethylamine (100 μl) in dry toluene (50 ml.) and refluxed for about 48 hours.

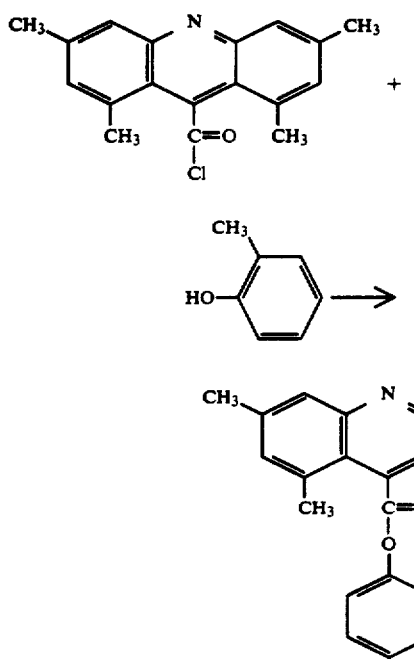

The reaction product

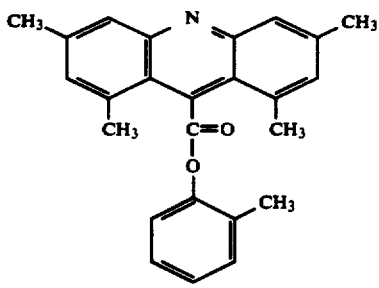

was washed with H₂O (and then aqueous saturated NaCl, dried over MgSO₄. After filteration solvent was removed go give a dark yellow oil (about 70%). It was purified by column chromatography to give a pure sample of

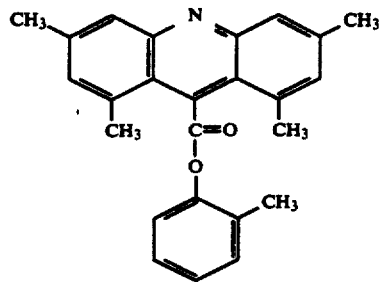

The compound was characterized by IR, M.S., and NMR.

IR(Nujol) shows carbonyl peak at 1745 cm.$^{-1}$
M.S.(FAB) shows M+ +1 peak at 370$^m/e$
NMR (250 MHz, δ, CDCl₃) shows aromatic peaks as doublet at 8.13 ppm and 8.10 ppm (1H), a singlet at 7.91 ppm (2H), multiplets from 7.39 ppm to 7.20 ppm (5H), and for others as three singlets at 2.78 ppm (6H), 2.55 ppm (6H) and 2.17 ppm (3H)

From the foregoing, it will be obvious to those skilled in the art that various modifications in the above-described compositions and methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A chemiluminescent label compound containing a fused ring system comprising a
   (i) wherein the fused ring contains a heterocyclic ring and is selected from the group consisting of acridinium benz[a]acridinium benz[b]acridinium, benz[c]acridinium, a benzimidazole cation, quinolinium, isoquinolinium, quinolizinium, and a cyclic substituted quinolinium, pyridinium, pyrimidininium, pyridazinium, pyrazininium, phenanthridinium, and quinoxalinium;
      (a) which fused ring's heterocyclic ring contains an available carbon atom in the heterocyclic ring that is adjacent to a carbon forming a fused ring with the heterocyclic ring; and
      (b) at least one substituent that is peri relative to said available carbon of the heterocyclic ring, which substituent serves to enhance the hydrolytic stability of the chemiluminescent label compound; and
   (ii) a leaving group coupled to the heterocyclic ring through a carbon adjacent to a fused ring carbon such that the leaving group and heterocyclic ring join to form a difunctional carboxy-containing linkage in which the carboxy carbon is directly bonded to the carbon of the heterocyclic ring adjacent to a fused ring carbon,
      (a) the linkage being an ester, thiolester or amide of a carboxylic acid, and
      (b) said linkage substituted heterocyclic ring is susceptible to chemical attack to dissociate the heterocyclic ring to a transient compound by first cleaving the linkage to dissociate the leaving group from the heterocyclic ring system followed by dissociation of the residual carbonyl from the linkage.

2. The chemiluminescent label compound of claim 1 wherein the chemical attack is oxidic or elemental oxygen attack.

3. The chemiluminescent label compound of claim 1 wherein the leaving group includes an aryl ring or ring system.

4. The chemiluminescent label compound of claim 3 wherein the aryl ring or ring system is ring carbon-bonded to the other end of the linking oxygen, sulfur or nitrogen of the ester, thiolester or amide, as the case may be.

5. The chemiluminescent label compound of claim 3 wherein the aryl ring may be unsubstituted or substituted.

6. The chemiluminescent label compound of claim 5 wherein the aryl ring is substituted and the substitution is chemically or electronically functional.

7. The chemiluminescent label compound of claim 6 wherein the aryl ring or ring system contains at least one substituent on a six-member ring.

8. The chemiluminescent label compound of claim 7 wherein the substituent on the six-member ring is one or more groups acting in concert with peri substitution on the heterocyclic ring system to sterically and electronically hinder hydrolysis of the ester, thiolester or amide linkage.

9. The chemiluminescent label compound of claim 8 wherein aryl group substituent is one or more ortho substituent groups.

10. The chemiluminescent label compound of claim 9 wherein the aryl substitution also comprises meta and/or para substituents that possess a specific level of electron withdrawing capacity.

11. The chemiluminescent label compound of claim 10 wherein the specific level of electron withdrawing capacity is a $\sigma_p$ value greater than 0 and less than 1.

12. A conjugate of a specific binding material and the chemiluminescent label compound of claim 1.

13. A conjugate of a specific binding material and the chemiluminescent label compound of claim 2.

14. A conjugate of a specific binding material and the chemiluminescent label compound of claim 3.

15. A conjugate of a specific binding material and the chemiluminescent label compound of claim 4.

16. A conjugate of a specific binding material and the chemiluminescent label compound of claim 5.

17. A conjugate of a specific binding material and the chemiluminescent label compound of claim 6.

18. A conjugate of a specific binding material and the chemiluminescent label compound of claim 7.

19. A conjugate of a specific binding material and the chemiluminescent label compound of claim 8.

20. A conjugate of a specific binding material and the chemiluminescent label compound of claim 9.

21. A conjugate of a specific binding material and the chemiluminescent label compound of claim 10.

22. A conjugate of a specific binding material and the chemiluminescent label compound of claim 11.

23. A hydrolytically stable heterocyclic composition capable of chemiluminescent properties by chemically-induced dissociation when labeled to a specific binding material, comprising (a) a sterically-hindered ester, thiolester or amide linkage moiety with enhanced hydrolytic stability, (b) a leaving group that comprises a portion of (a), (c) a heterocyclic organic ring moiety of a fused ring structure selected from the group consisting of acridinium, benz[a]acridinium, benz[b]acridinium, benz[c]acridinium, a benzimidazole cation, quinolinium, isoquinolinium, quinolizinium, and a cyclic substituted quinolinium, pyridinium, pyrimidininium, pyridazinium, pyrazininium, phenanthridinium, and quinoxalinium that comprises a portion of (a), in which (1) the carbonyl carbon of (a) is covalently bonded to a carbon atom (x) of (c) and the remaining free valence of (a) is carbon bonded to (b), and (4) (c) contains (i) at least one ring carbon atom adjacent to said ring carbon atom (x), (ii) a bulky group in a position peri to (x) and (iii) a ring member heteroatom in an oxidation state that provides such chemiluminescence properties.

24. A hydrolytically stable conjugate possessing chemiluminescent properties by chemical dissociation, comprising a chemiluminescent label bonded to a specific binding material that contains (a) a sterically-hindered ester, thiolester or amide linkage moiety with enhanced hydrolytic stability, (b) a leaving group that comprises a portion of (a), (c) a heterocyclic organic ring moiety that comprises a portion of (a), in which (1) the carbonyl carbon of (a) is covalently bonded to a carbon atom (x) of (c) and the remaining free valence of (a) is carbon bonded to (b), and (4) (c) contains (i) at least one ring carbon atom adjacent to said ring carbon atom (x), (ii) a bulky group in a position peri to (x) and (ii) a ring member heteroatom that is in an oxidation state whereby reaction of molecular oxygen or a peroxide with said composition forms an intermediate which decays to produce chemiluminescence.

25. A method for assaying the presence of an analyte in a sample which comprises contacting an analyte with the conjugate of claim 12, inducing chemiluminescence by decay of an intermediate dissociated from the conjugate, and measuring luminescence therefrom to assay the analyte.

26. A method for assaying the presence of an analyte in a sample which comprises contacting an analyte with the conjugate of claim 13, inducing chemiluminescence by decay of an intermediate dissociated from the conjugate, and measuring luminescence therefrom to assay the analyte.

27. A method for assaying the presence of an analyte in a sample which comprises contacting an analyte with the conjugate of claim 14, inducing chemiluminescence by decay of an intermediate dissociated from the conjugate, and measuring luminescence therefrom to assay the analyte.

28. A method for assaying the presence of an analyte in a sample which comprises contacting an analyte with the conjugate of claim 15, inducing chemiluminescence by decay of an intermediate dissociated from the conjugate, and measuring luminescence therefrom to assay the analyte.

29. A method for assaying the presence of an analyte in a sample which comprises contacting an analyte with the conjugate of claim 16, inducing chemiluminescence by decay of an intermediate dissociated from the conjugate, and measuring luminescence therefrom to assay the analyte.

30. A method for assaying the presence of an analyte in a sample which comprises contacting an analyte with the conjugate of claim 17, inducing chemiluminescence by decay of an intermediate dissociated from the conjugate, and measuring luminescence therefrom to assay the analyte.

31. A method for assaying the presence of an analyte in a sample which comprises contacting an analyte with the conjugate of claim 18, inducing chemiluminescence by decay of an intermediate dissociated from the conjugate, and measuring luminescence therefrom to assay the analyte.

32. A method for assaying the presence of an analyte in a sample which comprises contacting an analyte with the conjugate of claim 19, inducing chemiluminescence by decay of an intermediate dissociated from the conjugate, and measuring luminescence therefrom to assay the analyte.

33. A method for assaying the presence of an analyte in a sample which comprises contacting an analyte with the conjugate of claim 20, inducing chemiluminescence by decay of an intermediate dissociated from the conjugate, and measuring luminescence therefrom to assay the analyte.

34. A method for assaying the presence of an analyte in a sample which comprises contacting an analyte with the conjugate of claim 21, inducing chemiluminescence by decay of an intermediate dissociated from the conjugate, and measuring luminescence therefrom to assay the analyte.

35. A method for assaying the presence of an analyte in a sample which comprises contacting an analyte with the conjugate of claim 22, inducing chemiluminescence by decay of an intermediate dissociated from the conjugate, and measuring luminescence therefrom to assay the analyte.

36. A method for assaying the presence of an analyte in a sample which comprises contacting an analyte with the conjugate of claim 24, inducing chemiluminescence by decay of an intermediate dissociated from the conjugate, and measuring luminescence therefrom to assay the analyte.

37. A specific binding assay kit comprising a vial containing a conjugate possessing chemiluminescent properties by chemically induced dissociation and containing the conjugate of claim 12.

38. A specific binding assay kit comprising a vial containing a conjugate possessing chemiluminescent properties by chemically induced dissociation and containing the conjugate of claim 13.

39. A specific binding assay kit comprising a vial containing a conjugate possessing chemiluminescent properties by chemically induced dissociation and containing the conjugate of claim 14.

40. A specific binding assay kit comprising a vial containing a conjugate possessing chemiluminescent properties by chemically induced dissociation and containing the conjugate of claim 15.

41. A specific binding assay kit comprising a vial containing a conjugate possessing chemiluminescent properties by chemically induced dissociation and containing the conjugate of claim 16.

42. A specific binding assay kit comprising a vial containing a conjugate possessing chemiluminescent properties by chemically induced dissociation and containing the conjugate of claim 16.

43. A specific binding assay kit comprising a vial containing a conjugate possessing chemiluminescent properties by chemically induced dissociation and containing the conjugate of claim 17.

44. A specific binding assay kit comprising a vial containing a conjugate possessing chemiluminescent properties by chemically induced dissociation and containing the conjugate of claim 18.

45. A specific binding assay kit comprising a vial containing a conjugate possessing chemiluminescent properties by chemically induced dissociation and containing the conjugate of claim 19.

46. A specific binding assay kit comprising a vial containing a conjugate possessing chemiluminescent properties by chemically induced dissociation and containing the conjugate of claim 20.

47. A specific binding assay kit comprising a vial containing a conjugate possessing chemiluminescent properties by chemically induced dissociation and containing the conjugate of claim 21.

48. A specific binding assay kit comprising a vial containing a conjugate possessing chemiluminescent properties by chemically induced dissociation and containing the conjugate of claim 22.

49. A specific binding assay kit comprising a vial containing a conjugate possessing chemiluminescent properties by chemically induced dissociation and containing the conjugate of claim 24.

* * * * *